(12) United States Patent
Pitterna et al.

(10) Patent No.: US 7,795,442 B2
(45) Date of Patent: Sep. 14, 2010

(54) PREPARATION OF THIAZOLES

(75) Inventors: Thomas Pitterna, Stein (CH); Henry Szczepanski, Stein (CH); Peter Mainenfisch, Stein (CH); Ottmar Franz Huter, Lorrach (DE); Thomas Rapold, Munchwilen (CH); Marcel Senn, Basel (CH); Thomas Gobel, Lorrach (DE); Anthony Cornelius O'Sullivan, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/424,594

(22) Filed: Apr. 16, 2009

(65) Prior Publication Data

US 2009/0198054 A1    Aug. 6, 2009

Related U.S. Application Data

(62) Division of application No. 11/947,891, filed on Nov. 30, 2007, now Pat. No. 7,538,229, which is a division of application No. 11/552,255, filed on Oct. 24, 2006, now Pat. No. 7,323,564, which is a division of application No. 10/400,826, filed on Mar. 27, 2003, now Pat. No. 7,161,011, which is a division of application No. 09/331,433, filed as application No. PCT/EP97/07088 on Dec. 17, 1997, now Pat. No. 6,548,676.

(30) Foreign Application Priority Data

Dec. 19, 1996 (CH) ..................... 3125/96

(51) Int. Cl.
*C07D 277/32* (2006.01)
(52) U.S. Cl. .................................... 548/182
(58) Field of Classification Search ................... 548/182
See application file for complete search history.

(56) References Cited

U.S. PATENT DOCUMENTS 5,461,167 A    10/1995    Schiokawa et al.

FOREIGN PATENT DOCUMENTS

| EP | 192060 | 8/1986 |
| EP | 462573 | 12/1991 |

WO    9720829    6/1997

*Primary Examiner*—Rebecca L Anderson
(74) *Attorney, Agent, or Firm*—Rebecca A. Howard

(57) ABSTRACT

A process is provided for preparing compounds having the general formula I

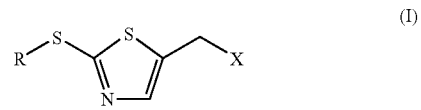

(I)

wherein R is a range of organic groups and X is a leaving group. The process comprises reacting a compound of formula II

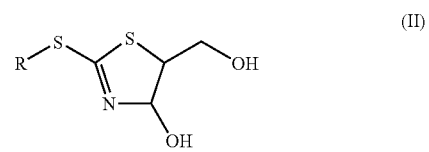

(II)

with a water-removing reagent. When X is halogen or a sulfonate, the compound of formula I may be prepared by reacting a compound of the formula III

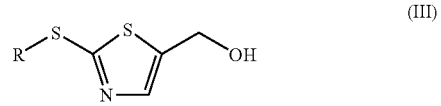

(III)

with a halogenating agent or a sulfonylating agent. Alternatively, when X is halogen, the compound of formula I can be prepared by reacting a compound of the formula IV

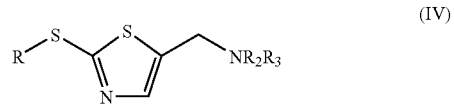

(IV)

where R2 and R2 are defined organic groups, with a compound of the formula halogen-C(=O)—O—C1-C8alkyl, halogen-C(=O)—O-aryl or halogen-C(=O)—O-benzyl.

1 Claim, No Drawings

PREPARATION OF THIAZOLES

This application is a divisional application of U.S. Ser. No. 11/947,891, filed Nov. 30, 2007, now U.S. Pat. No. 7,538,229, which is a divisional application of U.S. Ser. No. 11/552,255, filed Oct. 24, 2006, now U.S. Pat. No. 7,323,564, which is a divisional application of U.S. Ser. No. 10/400,826, filed Mar. 27, 2003, now U.S. Pat. No. 7,161,011, which is a divisional application of U.S. Ser. No. 09/331,433, filed Jun. 18, 1999, now U.S. Pat. No. 6,548,676, which is a National Stage entry of International Application No. PCT/EP97/07088 filed Dec. 17, 1997, which claims priority to CH 3125/96 filed Dec. 19, 1996, the contents of which are incorporated herein by reference.

The invention relates to a process for the preparation of a compound of the formula

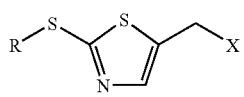

(I)

and, where applicable, its E/Z-isomers, mixtures of E/Z-isomers and/or tautomers and acid addition products thereof, in each case in free form or in salt form, wherein R is unsubstituted or substituted $C_1C_{12}$alkyl, unsubstituted or substituted $C_2$-$C_4$alkenyl, unsubstituted or substituted $C_2$-$C_4$alkynyl, unsubstituted or substituted $C_3$-$C_6$cycloalkyl, unsubstituted or substituted aryl, unsubstituted or substituted heteroaryl, or —$SR_1$;

$R_1$ is unsubstituted or substituted $C_1C_{12}$alkyl, unsubstituted or substituted $C_2$-$C_4$alkenyl, unsubstituted or substituted $C_2$-$C_4$alkenyl, unsubstituted or substituted $C_2$-$C_4$alkynyl, unsubstituted or substituted cycloalkyl, unsubstituted or substituted aryl or unsubstituted or substituted heteroaryl and X is a leaving group; which comprises a) reacting a compound of the formula

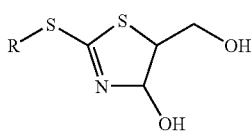

(II)

or, where applicable, an E/Z-isomer, a mixture of E/Z-isomers and/or a tautomer thereof, in each case in free form or in salt form, wherein R is as defined for formula (I), with a water removing reagent; or b) for the preparation of a compound of formula (I) wherein X is halogen or a sulfonate, reacting a compound of the formula

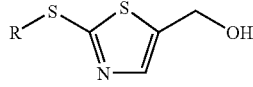

(III)

and, where applicable, its E/Z-isomers, mixtures of E/Z-isomers and/or tautomers and acid addition products thereof, in each case in free form or in salt form, wherein R is as defined for formula (I), with a halogenating agent or a sulfonylating agent; or c) for the preparation of a compound of formula (I) wherein X is halogen, reacting a compound of the formula

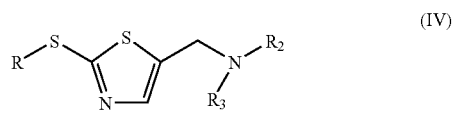

(IV)

and, where applicable, its E/Z-isomers, mixtures of E/Z-isomers and/or tautomers and acid addition products thereof, in each case in free form or in salt form, wherein R is as defined for formula (I); and $R_2$ and $R_3$ are each independently of the other H, $C_1$-$C_6$alkyl, $C_3$-$C_6$cycloalkyl, phenyl or benzyl or, together with the nitrogen atom to which they are bonded, form a five- to seven-membered ring in which a —$CH_2$— group has optionally been replaced by a hetero atom selected from the group consisting of O and S, or by $NR_9$, and wherein the carbon-chain of the five- to seven-membered ring is unsubstituted or is mono- or di-substituted by $C_1$-$C_4$alkyl; and $R_9$ is an organic radical;

with a compound of the formula halogen-C(=O)—O—$C_1$-$C_8$alkyl, halogen-C(=O)—O-aryl or halogen-C(=O)—O-benzyl, preferably with ethyl chloroformate;

and in each case, if desired, converting a compound of formula (I) obtainable in accordance with the process or by another method, or an E/Z-isomer or tautomer and acid addition products thereof, in each case in free form or in salt form, into a different compound of formula (I) or an E/Z-isomer or tautomer and acid addition products thereof, in each case in free form or in salt form, separating a mixture of E/Z-isomers obtainable in accordance with the process and isolating the desired isomer, and/or converting a free compound of formula (I) obtainable in accordance with the process or by another method, or an E/Z-isomer or tautomer thereof, into a salt or converting a salt, obtainable in accordance with the process or by another method, of a compound of formula (I) or of an E/Z-isomer or tautomer thereof into the free compound of formula (I) or an E/Z-isomer or tautomer thereof or into a different salt.

Methods of synthesis for the compounds of formula (I) are described in the literature. However, they are not completely satisfactory and there is therefore the need to make available improved processes for the preparation of those compounds. The compounds of formula (I) are valuable intermediates in the preparation of other compounds that can be used in the preparation of compounds—especially of formula (A) below having pesticidal activity. Accordingly, the invention relates also to a process for the preparation of a compound of the formula

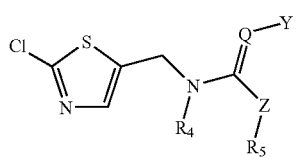

(A)

and, where applicable, their E/Z-isomers, mixtures of E/Z-isomers and/or tautomers and acid addition products thereof, in each case in free form or in salt form, wherein Q is CH or N, Y is $NO_2$ or CN, Z is $CHR_6$, O, $NR_6$ or S, $R_4$ and $R_5$ are either each independently of the other hydrogen or unsubstituted or $R_7$-substituted alkyl, or together form an alkylene bridge having two or three carbon atoms, and said alkylene bridge may additionally contain a hetero atom selected from the group consisting of $NR_8$, O and S;

$R_6$ is H or unsubstituted or $R_7$-substituted alkyl, $R_7$ is unsubstituted or substituted aryl or heteroaryl, and $R_8$ is H or $C_1$-$C_{12}$alkyl;

which comprises reacting a compound of formula (I), prepared by the process described above, with a compound of the formula

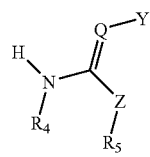

(B)

or, where applicable, an E/Z-isomer, a mixture of E/Z-isomers and/or a tautomer thereof, in each case in free form or in salt form, wherein Q, Y, Z, $R_4$ and $R_5$ are as defined above for formula (A), to form a compound of the formula

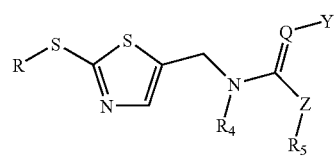

(C)

or, where applicable, an E/Z-isomer, a mixture of E/Z-isomers and/or a tautomer and acid addition products thereof, in each case in free form or in salt form, wherein R is as defined above for formula (I) and Q, Y, Z, $R_4$ and $R_5$ are as defined above for formula (A), and converting the compound of formula (C) by means of a halogenating agent into a compound of formula (A).

The present invention relates also to a process for the preparation of a compound of formula (C) and, where applicable, its E/Z-isomers, mixtures of E/Z-isomers and/or tautomers and acid addition products thereof, in each case in free form or in salt form, which comprises reacting a compound of the formula (I) with a compound of the formula (B); and a process for the preparation of a compound of formula (A) and, where applicable, its E/Z-isomers, mixtures of E/Z-isomers and/or tautomers and acid addition products thereof, in each case in free form or in salt form, which comprises reacting a compound of the formula: (C) with a halogenating agent.

Some compounds of formulae (I) to (VIII) and (A) to (C) defined hereinbefore and herein-after contain asymmetric carbon atoms, as a result of which the compounds may occur in optically active form. The corresponding formulae are intended to include all those possible isomeric forms as well as mixtures thereof, for example racemates or mixtures of E/Z-isomers.

The general terms used hereinbefore and hereinafter have the meanings given below, unless defined otherwise:

Unless defined otherwise, carbon-containing groups and compounds each contain from 1 up to and including 8, preferably from 1 up to and including 6, especially from 1 up to and including 4, more especially 1 or 2, carbon atoms.

Alkyl—both as a group per se and as a structural element of other groups and compounds, such as haloalkyl, arylalkyl or hydroxyalkyl—is preferably, in each case giving due consideration to the number of carbon atoms contained in the group or compound in question, either straight-chained, i.e. methyl, ethyl, propyl, butyl, pentyl or hexyl, or branched, for example isopropyl, isobutyl, sec-butyl, tert-butyl, isopentyl, neopentyl or isohexyl.

Alkenyl—both as a group per se and as a structural element of other groups and compounds, such as haloalkenyl or arylalkenyl—is, in each case giving due consideration to the number of carbon atoms contained in the group or compound in question, either straight-chained, for example vinyl, 1-methylvinyl, allyl, 1-butenyl or 2-hexenyl, or branched, for example isopropenyl.

Alkynyl—both as a group per se and as a structural element of other groups and compounds, such as haloalkynyl—is, in each case giving due consideration to the number of carbon atoms contained in the group or compound in question, either straight-chained, for example propargyl, 2-butynyl or 5-hexynyl, or branched, for example 2-ethynylpropyl or 2-propargylisopropyl.

$C_3$-$C_6$Cycloalkyl is cyclopropyl, cyclobutyl, cyclopentyl or cyclohexyl, especially cyclohexyl.

Aryl is phenyl or naphthyl, especially phenyl.

Heteroaryl is understood as being a five- to seven-membered monocyclic aromatic ring that contains from one to three hetero atoms selected from the group consisting of N, O and S, especially N and S, or a bicyclic heteroaryl that may contain either in only one ring—such as, for example, in quinolinyl, quinoxalinyl, indolinyl, benzothiophenyl or benzofuranyl—or in both rings—such as, for example, in pteridinyl or purinyl—independently of one another, one or more hetero atoms selected from N, O and S. Preference is given to pyridyl, pynmidinyl, thiazolyl and benzothiazolyl, especially thiazolyl.

Halogen—both as a group per se and as a structural element of other groups and compounds, such as haloalkyl, haloalkenyl and haloalkynyl—is fluorine, chlorine, bromine or iodine, especially fluorine, chlorine or bromine, more especially chlorine or bromine, very especially chlorine.

Halo-substituted carbon-containing groups and compounds, such as haloalkyl or haloalkenyl, may be partially halogenated or perhalogenated, the halogen substituents in the case of multi-halogenation being the same or different. Examples of haloalkyl—both as a group per se and as a structural element of other groups and compounds, such as haloalkenyl—are methyl substituted from one to three times by fluorine, chlorine and/or by bromine, such as $CHF_2$ or $CF_3$; ethyl substituted from one to five times by fluorine, chlorine and/or by bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or by bromine, such as $CH_2CHBrCH_2Br$, $CF_2CHFCF_3$, $CH_2CF_2CF_3$ or $CH(CF_3)_2$; and butyl or an isomer thereof substituted from one to nine times by fluorine, chorine and/or by bromine, such as $CF(CF_3)CHFCF_3$ or $CH_2(CF_2)_2CF_3$. Haloalkenyl is, for example, $CH_2CH\!=\!CHCl$, $CH_2CH\!=\!CCl_2$, $CH_2CF\!=\!CF_2$ or $CH_2CH\!=\!CHCH_2Br$.

Some compounds of formulae (I) to (VIII) and (A) to (C) may be in the form of tautomers. Therefore, hereinbefore and hereinafter those compounds are to be understood as including also the corresponding tautomers, even if the latter are not mentioned specifically in every case.

Compounds of formulae (I) to (VIII) and (A) to (C) that have at least one basic centre are able to form, for example, acid addition salts. These are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, $C_1$-$C_4$alkane-carboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, $C_1$-$C_4$alkane- or arylsulfonic acids, for example methane- or p-toluene-sulfonic acid. Moreover, compounds of formulae (I) to (IV) and (A) to (C) having at least one acid group, for example wherein R is —$CH_2$—COO-M, are able to form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or tri-hydroxy-lower alkylamine, for example mono-, di- or tri-ethanolamine. Furthermore, corresponding internal salts may be formed. Hereinbefore and hereinafter, the compounds of formula (I) are to be understood as being both the compounds of formulae (I) to (VIII) and (A) to (C) in free form and the corresponding salts. The same applies to tautomers of compounds of formulae (I) to (VIII) and (A) to (C) and their salts. Preference is in each case generally given to a process for the preparation of the free form.

Add addition products are understood as being products which are obtainable by the addition of an acid, preferably an inorganic acid, to a double bond, especially to a double bond of a heterocycle. For example, addition of an acid $HX_1$, wherein the anion $X_1$ has the meanings as given for X in formula (I), to a compound of the formula (I) as defined above may result in the compound of the formula

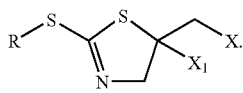

(IX)

The artisan is well aware, that an acid $HX_1$ can easily be split off from the said acid addition product; e.g. the compound of the formula (IX) can be converted into the compound of the formula (I). Therefore, the compounds of formula (I), (III), (IV), (VI) to (VIII), (A) and (C) are hereinbefore and hereinafter to be understood as being both the compounds of the formulae (I), (III), (IV), (VI) to (VIII), (A) and (C) and the corresponding acid addition products, in free form and the salts thereof, even if not all the forms are specifically mentioned in every case.

Hereinbefore and hereinafter a leaving group is understood as being any removable group that is customarily suitable in chemical reactions, such as is known to the person skilled in the art; for example halides, especially chloride or bromide, $H_2O$, SH, CN, sulfonates, sulfinates, $NO_3$, $NO_2$ or $SO_3$; special preference is given to chloride or bromide and sulfonates. Especially preferred leaving groups are mentioned in the individual processes.

Within the scope of the invention preference is given to the processes mentioned hereinbefore and hereinafter for the preparation of compounds of formulae (I) to (IV) and (VI) wherein (1) R is unsubstituted or halo- or hydroxy-substituted $C_1$-$C_{12}$alkyl, unsubstituted or halo-substituted aryl-$C_1$-$C_4$alkyl, unsubstituted or halo-substituted heteroaryl-$C_1$-$C_4$alkyl, aryl$C_2$-$C_4$alkenyl, heteroaryl-$C_2$-$C_4$alkenyl, unsubstituted or halo-substituted $C_2$-$C_4$alkenyl, $C_2$-$C_4$-alkynyl, aryl-$C_2$-$C_4$alkynyl, heteroaryl-$C_2$-$C_4$alkyflyl, $C_4$-$C_6$cycloalkyl, unsubstituted or halo-substituted aryl, unsubstituted or halo-substituted heteroaryl, —$CH_2$—COO—$C_1$-$C_8$alkyl, —$CH_2$—CO—$C_1$-$C_8$alkyl, $SR_1$ or —$CH_2$—COO-M, wherein M is hydrogen or a cation; especially $C_1$-$C_4$alkyl, hydroxy-$C_1$-$C_4$alkyl, $C_3$-$C_4$alkenyl, $C_3$-$C_4$alkynyl, chloro-$C_3$-$C_4$alkynyl, unsubstituted or chlorine-substituted phenyl, unsubstituted or chlorine-substituted benzyl, heteroaryl, cyclohexyl, —$CH_2$—COO—$C_1$-$C_4$alkyl more especially $C_1$-$C_4$alkyl, phenyl, benzyl, cyclohexyl, benzothiazol-2-yl or —$CH_2$—COO-ethyl; very especially phenyl or benzyl;

(2) X is methylsulfonate, trifluoromethylsulfonate, p-toluenesulfonate or halogen, especially chlorine or bromine;

(3) R is —$(CH_2)_n$—$SR_1$, and $R_1$ is $C_1$-$C_8$alkyl, aryl-$C_1$-$C_4$alkyl, heteroaryl-$C_1$-$C_4$alkyl, $C_2$-$C_4$alkenyl, aryl-$C_2$-$C_4$alkenyl, heteroaryl-$C_2$-$C_4$alkenyl, $C_2$-$C_4$alkynyl, aryl-$C_2$-$C_4$alkynyl, heteroaryl-$C_2$-$C_4$alkynyl, cyclohexyl, aryl, arylthio, heteroaryl, heteroarylthio; or heteroaryl or heteroarylthio which are both substituted with —$CH_2$—$X_1$ or formyl;

$X_1$ is as defined in claim 1 for X;

and n is 1 to 8;

especially $R_1$ is $C_1$-$C_4$alkyl, cyclohexyl, aryl or

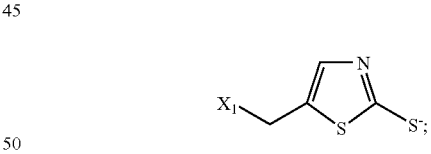

$X_1$ is halogen or hydroxy; and n is 1 or 2.

Also preferred are compounds of the formula (IV), wherein (4) $R_2$ and $R_3$ independently of each other are H, $C_1$-$C_6$-alkyl, $C_3$-$C_6$-cycloalkyl, phenyl or benzyl, or together with the N-atom to which they are bonded form a five- to seven-membered ring, wherein one $CH_2$-group may be replaced by a heteroatom selected from the group consisting of O and S, or by $NR_9$, and wherein the carbon-chain of the five- to seven-membered ring may be substituted by one or two $C_1$-$C_4$-alkyl groups; and $R_9$ is H, $C_1$-$C_6$-alkyl, $C_3$-$C_6$-cycloalkyl, phenyl or benzyl;

especially wherein $R_2$ and $R_3$ are independently of each other H, $C_1$-$C_6$-alkyl or $C_3$-$C_6$-cycloalkyl, or together with the N-atom to which they are bonded form a five- to seven-membered ring, wherein one $CH_2$-group may be replaced by a heteroatom selected from the group consisting of O and S, or by $NR_9$, and $R_9$ is H, $C_1$-$C_6$-alkyl, $C_3$-$C_6$-cycloalkyl, phenyl or benzyl;

especially wherein $R_2$ and $R_3$ are independently of each other is $C_1$-$C_6$-alkyl, or together with the N-atom to which they are bonded form a five- to seven-membered ring, wherein one $CH_2$-group may be replaced by a heteroatom selected from the group consisting of O and S, or by $NR_9$, and $R_9$ is $C_1$-$C_6$-alkyl, $C_3$-$C_6$-cycloalkyl, phenyl or benzyl;

very especially wherein $R_2$ and $R_3$ are independently of each other are $C_1$-$C_4$-Alkyl, or together form —$CH_2$—$CH_2$—$CH_2$—$CH_2$—, —$CH_2$—$CH_2$—$CH_2$—$CH_2$—$CH_2$—, —$CH_2$—$CH_2$—O—$CH_2$—$CH_2$— or —$CH_2$—$CH_2$—N($R_9$)—$CH_2$—$CH_2$—, and $R_9$ is $C_1$-$C_6$-alkyl, phenyl or benzyl.

Within the scope of the invention preference is given to a process for the preparation of a compound of formulae (A) and (C) wherein (5) $R_4$ and $R_5$ are either each independently of the other hydrogen or unsubstituted or $R_7$-substituted alkyl, or together form an alkylene bridge having two or three carbon atoms, and said alkylene bridge may additionally contain a group $NR_8$ or a hetero atom selected from the group consisting of O and S; and $R_8$ is $C_1$-$C_4$alkyl;

especially, $R_4$ and $R_5$ are each hydrogen or together form a two- or three-membered alkylene bridge that may additionally contain a hetero atom from the group consisting of $NR_8$ and O, and $R_8$ is methyl or ethyl;

more especially, $R_4$ and $R_5$ together are —$CH_2$—O—$CH_2$—, —$CH_2$—$CH_2$—$CH_2$— or —$CH_2$—$CH_2$—. The present invention relates also to a process for the preparation of a compound of formula (II) and, where applicable, its E/Z-isomers, mixtures of E/Z-isomers and/or tautomers, in each case in free form or in salt form, which comprises d) reacting a compound of the formula

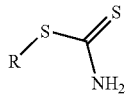
(V)

or, where applicable, an E/Z-isomer, a mixture of E/Z-isomers and/or a tautomer thereof, in each case in free form or in salt form, which is known or can be prepared by methods known per se and wherein R is as defined for formula (I), with glycidyl aldehyde of the formula

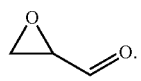

and in each case, if desired, converting a compound of formula (II) obtainable in accordance with the process or by another method, or an E/Z-isomer or tautomer thereof, in each case in free form or in salt form, into a different compound of formula (II) or an E/Z-isomer or tautomer thereof, in each case in free form or in salt form, separating a mixture of E/Z-isomers obtainable in accordance with the process and isolating the desired isomer, and/or converting a free compound of formula (II) obtainable in accordance with the process or by another method, or an E/Z-isomer or tautomer thereof, into a salt or converting a salt, obtainable in accordance with the process or by another method, of a compound of formula (II) or of an E/Z-isomer or tautomer thereof into the free compound of formula (II) or an E/Z-isomer or tautomer thereof or into a different salt.

The present invention relates also to a process for the preparation of a compound of formula (III) and, where applicable, its E/Z-isomers, mixtures of E/Z-isomers and/or tautomers and acid addition products thereof, in each case in free form or in salt form, which comprises either e) reacting a compound of formula (II) or, where applicable, an E/Z-isomer, a mixture of E/Z-isomers and/or a tautomer thereof, in each case in free form or in salt form, with an acid, or f) reacting a compound of the formula

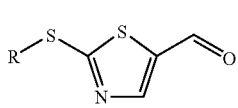
(VI)

and, where applicable, its E/Z-isomers, mixtures of E/Z-isomers and/or tautomers and acid addition products thereof, in each case in free form or in salt form, wherein R is as defined for formula (I), with hydrogen in the presence of a hydrogenation catalyst, and in each case, if desired, converting a compound of formula (III) obtainable in accordance with the process or by another method, or an E/Z-isomer or tautomer thereof, in each case in free form or in salt form, into a different compound of formula (III) or an E/Z-isomer or tautomer thereof, in each case in free form or in salt form, separating a mixture of E/Z-isomers obtainable in accordance with the process and isolating the desired isomer, and/or converting a free compound of formula (III) obtainable in accordance with the process or by another method, or an E/Z-isomer or tautomer thereof, into a salt or converting a salt, obtainable in accordance with the process or by another method, of a compound of formula (III) or of an E/Z-isomer or tautomer thereof into the free compound of formula (III) or an E/Z-isomer or tautomer thereof or into a different salt.

The present invention relates also to a process for the preparation of a compound of formula (IV) and, where applicable, its E/Z-isomers, mixtures of E/Z-isomers and/or tautomers, in each case in free form or in salt form, wherein R, $R_1$, $R_2$ and $R_3$ are as defined above for compounds of formulae (I) and (IV), which comprises g) reacting a compound of the formula

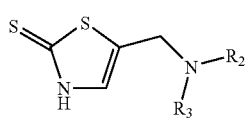
(VII)

and, where applicable, its E/Z-isomers, mixtures of E/Z-isomers and/or tautomers and acid addition products thereof, in each case in free form or in salt form, which is known or can be prepared by methods known per se and wherein $R_2$ and $R_3$ are as defined above for formula (IV), with a compound of the formula R—$X_2$, which is known or can be prepared by methods known per se and wherein R is as defined in formula (I) and $X_2$ is a leaving group, such as an alkyl-, haloalkyl- or aryl-sulfonate or halogen, especially bromine or chlorine;

and in each case, if desired, converting a compound of formula (IV) obtainable in accordance with the process or by another method, or an E/Z-isomer or tautomer thereof, in each case in free form or in salt form, into a different compound of formula (IV) or an E/Z-isomer or tautomer thereof, in each case in free form or in salt form, separating a mixture of E/Z-isomers obtainable in accordance with the process and isolating the desired isomer, and/or converting a free compound of formula (IV) obtainable in accordance with the process or by another method, or an E/Z-isomer or tautomer thereof, into a salt or converting a salt, obtainable in accordance with the process or by another method, of a compound of formula (IV) or of an E/Z-isomer or tautomer thereof into the free compound of formula (IV) or an E/Z-isomer or tautomer thereof or into a different salt.

The present invention relates also to a process for the preparation of a compound of formula (VI) and, where applicable, its E/Z-isomers, mixtures of E/Z-isomers and/or tautomers, in each case in free form or in salt form, which comprises h) formulating a compound of the formula

(VIII)

or, where applicable, an E/Z-isomer, a mixture of E/Z-isomers and/or a tautomer and acid addition products thereof, in each case in free form or in salt form, which is known or can be prepared by methods known per se and wherein R is as defined above for formula (I), and in each case, if desired, converting a compound of formula (VI) obtainable in accordance with the process or by another method, or an E/Z-isomer or tautomer thereof, in each case in free form or in salt form, into a different compound of formula (VI) or an E/Z-isomer or tautomer thereof, in each case in free form or in salt form, separating a mixture of E/Z-isomers obtainable in accordance with the process and isolating the desired isomer, and/or converting a free compound of formula (VI) obtainable in accordance with the process or by another method, or an E/Z-isomer or tautomer thereof, into a salt or converting a salt, obtainable in accordance with the process or by another method, of a compound of formula (VI) or of an E/Z-isomer or tautomer thereof into the free compound of formula (VI) or an E/Z-isomer or tautomer thereof or into a different salt.

With regard to the E/Z-isomers and tautomers, in free form or in salt form, of the starting materials of formulae (II) to (VIII) mentioned hereinbefore and hereinafter, the statements made above with respect to the E/Z-isomers and tautomers, in free form or in salt form, of the compounds of formula (I) apply analogously.

The reactions of variants a) to h) described hereinbefore and hereinafter are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately −20° C. to approximately +120° C., especially from 20° C. to 80° C., and, if necessary, in a closed vessel, under pressure, under an inert gas atmosphere and/or under anhydrous conditions. Especially advantageous reaction conditions can be taken from the Examples.

The reactants can in each case be reacted with one another as such, i.e. without the addition of a solvent or diluent, for example in the molten state. However, the addition of an inert solvent or diluent or of a mixture thereof is in most cases advantageous. There may be mentioned as examples of such solvents and diluents: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction in question is carried out in the presence of a base, bases such as triethylamine, pyridine, N-methylmorpholine or N,N-diethylaniline in excess may also serve as solvent or diluent. If the reaction is carried out in the presence of an acid catalyst, acids, for example strong organic carboxylic acids, such as unsubstituted or substituted, e.g. halo-substituted, $C_1$-$C_4$alkanecarboxylic acids, for example formic acid, acetic acid or propionic acid, in excess may also serve as solvent or diluent. Suitable solvents for the reaction in question can be taken from the Examples given below.

Variant (a):

The reaction is preferably carried out in a temperature range of from −20 to 160° C., especially from 0 to 100° C., customarily at from 25 to 50° C.

Suitable solvents are especially: aliphatic and aromatic hydrocarbons, halogenated hydrocarbons, esters, nitriles, ethers; for example: petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, diethyl ether, diisopropyl ether, tetrahydrofuran, dioxane; or a mixture thereof; especially methylene chloride.

There are suitable as reagents especially water-removing, halide-containing agents, such as thionyl chloride ($SOCl_2$), thionyl bromide ($SOBr_2$), phosphorus oxychloride ($POCl_3$), phosphorus oxybromide ($POBr_3$), phosphorus pentachloride or a sulfonic acid chloride or bromide; thionyl chloride is preferred.

Water or a base may be added to the reaction mixture, if desired; especially suitable bases are, for example, alkali metal or alkaline earth metal carbonates, alkali metal or alkaline earth metal hydrogen carbonates or alkali metal or alkaline earth metal hydroxides, or a tertiary amine; in a preferred form the reaction is carried out without the addition of a base.

Variant (b):

The reaction is preferably carried out in a temperature range of from −20 to 160° C., especially from 0 to 100° C., customarily from 0 to 25° C.

Suitable solvents are especially: aliphatic and aromatic hydrocarbons, halogenated hydrocarbons, esters, nitriles, ethers; for example: petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, diethyl ether, diisopropyl ether, tetrahydrofuran, dioxane; or a mixture thereof; methylene chloride is preferred.

Reagents: halide-containing water-removing agent, or sulfonylating agent; for example: thionyl chloride, phosphorus oxychloride, phosphorus pentachloride, phosphorus oxytnbromide, triphenylphosphine+bromine; or a sulfonic acid chloride or anhydride; customarily: thionyl chloride, triphenylphosphifle+bromine, toluenesulfonyl chloride, methanesulfonyl chloride, trifluoromethanesulfonyl chloride or methanesulfonyl anhydride.

Water or a base may be added to the reaction mixture, if desired; especially suitable bases are, for example, alkali metal or alkaline earth metal carbonates, alkali metal or alkaline earth metal hydrogen carbonates or alkali metal or alkaline earth metal hydroxides, or a tertiary amine; in a preferred form the reaction is carried out without additives.

Variant (c):

The reaction is preferably carried out in a temperature range of from −20 to 160° C., especially from 0 to 100° C., preferably from 50 to 70° C.

Suitable solvents are especially: aliphatic and aromatic hydrocarbons, halogenated hydrocarbons, esters, nitriles, ethers; for example: petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, diethyl ether, diisopropyl ether, tetrahydrofuran, dioxane; or a mixture thereof; tetrahydrofuran is especially preferred.

Variant (d):

The reaction is preferably carried out in a temperature range of from −20 to 160° C., especially from 0 to 100° C., preferably from 0 to 25° C.

Suitable solvents are especially: aliphatic and aromatic hydrocarbons, halogenated hydrocarbons, esters, amides, nitriles, ethers, alcohols, water, for example: petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, diethyl ether, dimethylformamide, dimethylacetamide, diisopropyl ether, tetrahydrofuran, dioxane, ethanol, methanol, isopropanol, water, or a mixture thereof; a mixture of water and ethanol is preferred.

An acid, a base or a buffer may be added to the reaction mixture, if desired; preference is given to a buffer having a pH of from 6 to 8, especially a phosphate buffer having a pH value of 7.

Variant (e):

The reaction is preferably carried out in a temperature range of from −20 to 160° C., especially from 0 to 100° C., preferably from 25 to 50° C.

Suitable solvents are especially: aliphatic and aromatic hydrocarbons, halogenated hydrocarbons, esters, amides, nitriles, ethers, alcohols, water, for example: petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, diethyl ether, dimethylformamide, dimethylacetamide, diisopropyl ether, tetrahydrofuran, dioxane, ethanol, methanol, isopropanol, water, or a mixture thereof; a mixture of water and ethanol is preferred.

Preferred acids for carrying out the reaction are inorganic acids, such as hydrochloric acid, hydrobromic acid, sulfuric acid, phosphoric acid, perchloric acid, tetrafluoroboric acid; carboxylic acids, such as trifluoroacetic acid; or sulfonic acids, such as toluenesulfonic acid, benzenesulfonic acid, camphorsulfonic acid; hydrochloric acid is preferred.

Variant (f):

The reaction is preferably carried out in a temperature range of from −20 to 160° C., especially from 0 to 100° C., preferably from 0 to 25° C.

Suitable solvents are especially: hydrocarbons, esters, amides, nitriles, ethers, water; petroleum ether, pentane, hexane, heptane, ethyl acetate, acetonitrile, diethyl ether, dimethylformamide, dimethylacetamide, diisopropyl ether, tetrahydrofuran, dioxane, water; or a mixture thereof; ethyl acetate is preferred.

Suitable hydrogenation catalysts are, for example: metals or metal oxides, especially those of transition metals, especially also those on an inert support material; platinum oxide and nickel, especially platinum oxide, are preferred. A Lewis acid is customarily added to the reaction mixture; especially suitable are halides of transition metals, especially iron(II) chloride.

Variant (g):

The reaction is preferably carried out in a temperature range of from −20 to 160° C., especially from 0 to 100° C., preferably from 50 to 80° C.

Suitable solvents are especially: aliphatic and aromatic hydrocarbons, halogenated hydrocarbons, esters, amides, nitriles, ethers, alcohols, water, for example: petroleum ether, pentane, hexane, heptane, chlorobenzene, methylene chloride, ethylene chloride, bromochloromethane, chloroform, carbon tetrachloride, tetrachloroethylene, ethyl acetate, acetonitrile, diethyl ether, dimethylformamide, dimethylacetamide, diisopropyl ether, tetrahydrofuran, dioxane, ethanol, methanol, isopropanol, water, or a mixture thereof; acetonitrile is preferred.

Suitable alkylating agents are especially unsubstituted or substituted alkyl halides or sulfonates; substituted or unsubstituted benzyl chloride, bromide, mesylate or tosylate; substituted or unsubstituted allyl chloride, bromide, mesylate or tosylate; substituted or unsubstituted propargyl chloride, bromide, mesylate or tosylate; esters or amides of bromoacetic acid or chloroacetic acid; especially benzyl chloride, benzyl bromide, ethyl chloroacetate, ethyl bromoacetate, allyl chloride, propargyl chloride; benzyl bromide is especially preferred.

Bases may be added to the reaction medium, if desired. Especially suitable are alkali metal or alkaline earth metal carbonates, hydrogen carbonates or hydroxides, or a tertiary amine; potassium carbonate is especially preferred.

Variant (h):

The reaction is preferably carried out in a temperature range of from −20 to 160° C., especially from 0 to 100° C., preferably from 25 to 50° C.

Suitable solvents are especially: aliphatic and aromatic hydrocarbons, halogenated hydrocarbons, ethers; for example: petroleum ether, pentane, hexane, heptane. chlorobenzene, methylene chloride, ethylene chloride, bromochloromethane, chloroform, carbon tetrachloride, tetrachloroethylene, diethyl ether, diisopropyl ether, tetrahydrofuran, dioxane; or a mixture thereof; it is especially preferred to carry out the process without a solvent.

There is preferably used as the reagent a mixture of phosphorus oxychloride and dimethylformamide.

Salts of compounds of formulae (I) to (IV), (VI) and (A) to (C) can be prepared in a manner known per se. For example, acid addition salts are obtained by treatment with a suitable acid or a suitable ion exchange reagent, and salts with bases are obtained by treatment with a suitable base or a suitable ion exchange reagent.

Salts of compounds of formulae (I) to (IV), (VI) to (VIII) and (A) to (C) can be converted into the corresponding free compounds in customary manner; acid addition salts, for example, by treatment with a suitable basic agent or a suitable ion exchange reagent, and salts with bases, for example, by treatment with a suitable acid or a suitable ion exchange reagent.

Salts of compounds of formulae (I) to (IV), (VI) to (VIII) and (A) to (C) can be converted into different salts of compounds of the corresponding formulae in a manner known per se; acid addition salts, for example, can be converted into different acid addition salts, for example by treating a salt of an inorganic acid, such as a hydrochloride, with a suitable metal salt, such as a sodium, barium or silver salt, of an acid, for example silver acetate, in a suitable solvent in which an inorganic salt that forms, for example silver chloride, is insoluble and therefore separates out of the reaction mixture.

Depending on the procedure and the reaction conditions, the compounds of formulae (I) to (IV), (VI) to (VIII) and (A) to (C) having salt-forming properties can be obtained in free form or in the form of salts.

The compounds of formulae (I) to (IV), (VI) to (VIII) and (A) to (C) and in each case, where applicable, their tautomers, in each case in free form or in salt form, may be in the form of one of the possible isomers or in the form of a mixture thereof, for example, depending on the number of asymmetric carbon atoms occurring in the molecule and their absolute and relative configuration, and/or depending on the configuration of non-aromatic double bonds occurring in the molecule, in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and is to be interpreted as such hereinbefore and hereinafter, even if stereochemical details are not mentioned specifically in every case.

Mixtures of enantiomers, such as racemates, that are obtainable in a corresponding manner can be resolved into the optical antipodes by known methods, for example by recrystallisation from an optically active solvent, by chromatography on chiral adsorbants, for example high pressure liquid chromatography (HPLC) on acetylcellulose, with the aid of suitable microorganisms, by cleavage with specific, immobilised enzymes, via the formation of inclusion compounds, for example using chiral crown ethers, only one enantiomer being complexed, or by conversion into diastereoisomeric salts, for example by reaction of a basic end-product racemate with an optically active acid, such as a carboxylic acid, for example camphoric, tartaric or malic acid, or a sulfonic acid, for example camphorsulfonic acid, and separation of the mixture of diastereoisomers so obtained, for example on the basis of their different solubilities by fractional crystallisation, into the diastereoisomers, from which the desired enantiomer can be freed by the action of suitable, for example basic, agents.

Mixtures of diastereoisomers and mixtures of racemates of compounds of formulae (I) to (IV), (VI) to (VIII) and (A) to (C) which may be obtained by the process according to the starting materials and procedures chosen, or which are obtainable by another method, or their salts, can be separated into the pure diastereoisomers or racemates in known manner on the basis of the physico-chemical differences between the constituents, for example by means of fractional crystallisation, distillation and/or chromatography.

Apart from by separation of corresponding mixtures of isomers, pure diastereoisomers and enantiomers can be obtained according to the invention also by generally known methods of diastereoselective and enantioselective synthesis, for example by carrying out the process according to the invention using starting materials having correspondingly suitable stereochemistry.

The compounds of formulae (I) to (IV), (VI) to (VIII) and (A) to (C) and their salts can also be obtained in the form of their hydrates and/or include other solvents, for example solvents that may have been used for the crystallisation of compounds that occur in solid form.

The invention relates to all those forms of the process according to which a compound obtainable as starting material or intermediate at any stage of the process is used as starting material and all or some of the remaining steps are carried out, or a starting material is used in the form of a derivative or salt and/or in the form of its racemates or antipodes or, especially, is formed under the reaction conditions.

Compounds of formulae (I) to (IV) and (A) to (C) obtainable in accordance with the process or by another method can be converted into different compounds of formulae (I) to (IV) and (A) to (C) in a manner known per se.

In the processes of the present invention there are preferably used those starting materials and intermediates, in each case in free form or in salt form, which lead to the compounds of formulae (I) to (IV), (VI) to (VIII) and (A) to (C) described at the beginning as being especially valuable, their salts or their acid addition products.

The invention relates especially to the preparation processes described in preparation processes P1 to P5.

The present invention relates also to the compounds of formula (II) and, where applicable, their E/Z-isomers, mixtures of E/Z-isomers and/or tautomers, in each case in free form or in salt form, wherein A is as defined above for formula (I).

The present invention relates also to the compounds of formula (III) and, where applicable, their E/Z-isomers, mixtures of E/Z-isomers and/or tautomers, in each case in free form or in salt form, wherein A is as defined above for formula (I).

The present invention relates also to the compounds of formula (IV) and, where applicable, their E/Z-isomers, mixtures of E/Z-isomers and/or tautomers, in each case in free form or in salt form, wherein R, $R_2$ and $R_3$ are as defined above. Preference is given to compounds of formula (IV) wherein $R_2$ and $R_3$ are each independently of the other $C_1$-$C_4$alkyl or two radicals $R_2$ and $R_3$, together with the nitrogen atom to which they are bonded, form a five- or six-membered ring in which a —$CH_2$— group has optionally been replaced by a hetero atom selected from the group consisting of O and S, or by NH, and wherein the five- or six-membered ring is unsubstituted or is mono- or di-substituted by $C_1$-$C_4$alkyl; especially, $R_2$ and $R_3$ together form —$(CH_2)_5$— or —$(CH_2)_2$—O—$(CH_2)_2$—.

The present invention relates also to the compounds of formula (VI) and, where applicable, their E/Z-isomers, mixtures of E/Z-isomers and/or tautomers, in each case in free form or in salt form, wherein R is as defined above for formula (I), with the proviso that A is not unsubstituted $C_1$-$C_2$alkyl.

For substituents R in the compounds of formulae (II), (III), (IV) and (VI) and in the compound R—$X_2$, the same preferred meanings as mentioned above in the processes for the preparation of the compounds of formula (I) apply.

The compounds of formulae (A), (B) and (C) are known.

PREPARATION EXAMPLES

Example P1a

2-Benzylsulfanyl-thiazole-5-carbaldehyde 180 mg of dimethylformamide and 130 mg of phosphorus oxychloride are added at room temperature to 200 mg of 2-benzylmercaptothiazole, and the mixture is stirred at 40° C. for 6 hours. Ice-water is then added to the reaction mixture, extraction with ethyl acetate is carried out, and the organic phase is dried over sodium sulfate and concentrated in vacuo.

Column chromatography on silica gel yields 2-benzylsulfanyl-thiazole-5-carbaldehyde in the form of an oil (compound 1.1).

Example P1b

The other compounds listed in Table 1 can also be prepared in a manner analogous to that described in Example P1a.

TABLE 1

Compounds of the formula

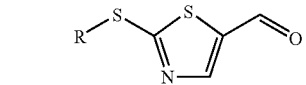

| Comp. No. | R | Physical data |
|---|---|---|
| 1.1 | benzyl | oil |
| 1.2 | phenyl | |
| 1.3 | cyclohexyl | |
| 1.4 | 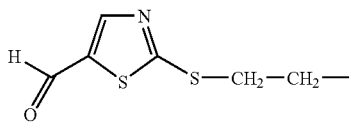 | |
| 1.5 | $CH_2$=CH—$CH_2$— | |
| 1.6 | ClCH=CH—$CH_2$— | |
| 1.7 | $CH_2$=C($CH_3$)—$CH_2$— | |
| 1.8 | $CH_2$=CH—$CH_2$—$CH_2$— | |
| 1.9 | 2-chlorobenzyl | |
| 1.10 | 4-chlorobenzyl | |
| 1.11 | CH≡C—$CH_2$— | |
| 1.12 | isopropyl | |
| 1.13 | $C_2H_5$—OC(=O)—$CH_2$— | |

TABLE 1-continued

Compounds of the formula

| Comp. No. | R | Physical data |
|---|---|---|
| 1.14 | (2-methylbenzothiazole structure) | |
| 1.15 | n-$C_3H_7$— | |
| 1.16 | HO—$CH_2$—$CH_2$— | |
| 1.17 | tert-butyl | |
| 1.18 | n-$C_{12}H_{25}$— | |
| 1.19 | 2-ethyl-pentyl | |

Example P2a 4-(2-Benzylsulfanyl-thiazol-5-ylmethyl)-morpholine 1.2 g of 5-morpholin-4-ylmethyl-3H.-thiazole-2-thione and 2.0 g of potassium carbonate are placed in 50 ml of acetonitrile; 1.0 g of benzyl bromide is added and stirring is then carried out at 70° C. for 90 minutes. The mixture is allowed to cool and is filtered, and the solvent is removed by evaporation. The residue crystallises from diisopropyl ether. In that manner 4-(2-benzylsulfanyl-thiazol-5-ylmethyl)-morpholine having a melting point of 103-104° C. is obtained (compound 2.1).

Example P2b

The other compounds listed in Table 2 can also be prepared in a manner analogous to that described in Example P2a.

TABLE 2

Compounds of the formula

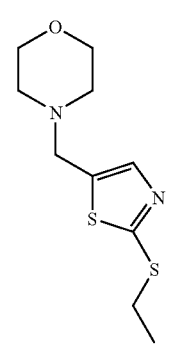

| Comp. No. | R | $R_2$ | $R_3$ | melting point |
|---|---|---|---|---|
| 2.1 | benzyl | —$CH_2$—$CH_2$—O—$CH_2$—$CH_2$— | | 103-104° C. |
| 2.2 | phenyl | —$CH_2$—$CH_2$—O—$CH_2$—$CH_2$— | | |
| 2.3 | cyclohexyl | —$CH_2$—$CH_2$—O—$CH_2$—$CH_2$— | | |
| 2.4 | (morpholinylmethyl-thiazole-ethylthio structure) | —$CH_2$—$CH_2$—O—$CH_2$—$CH_2$— | | |

TABLE 2-continued

Compounds of the formula $$R-S-\underset{N}{\underset{\|}{\overset{S}{\bigvee}}}-CH_2-N(R_2)(R_3)$$

| Comp. No. | R | $R_2$ | $R_3$ | melting point |
|---|---|---|---|---|
| 2.5 | $CH_2=CH-CH_2-$ | $-CH_2-CH_2-O-CH_2-CH_2-$ | | |
| 2.6 | $ClCH=CH-CH_2-$ | $-CH_2-CH_2-O-CH_2-CH_2-$ | | |
| 2.7 | $CH_2=C(CH_3)-CH_2-$ | $-CH_2-CH_2-O-CH_2-CH_2-$ | | |
| 2.8 | $CH_2=CH-CH_2-CH_2-$ | $-CH_2-CH_2-O-CH_2-CH_2-$ | | |
| 2.9 | 2-chlorobenzyl | $-CH_2-CH_2-O-CH_2-CH_2-$ | | |
| 2.10 | 4-chlorobenzyl | $-CH_2-CH_2-O-CH_2-CH_2-$ | | |
| 2.11 | $CH\equiv C-CH_2-$ | $-CH_2-CH_2-O-CH_2-CH_2-$ | | |
| 2.12 | isopropyl | $-CH_2-CH_2-O-CH_2-CH_2-$ | | |
| 2.13 | $C_2H_5-OC(=O)-CH_2-$ | $-CH_2-CH_2-O-CH_2-CH_2-$ | | |
| 2.14 | 2-methyl-benzothiazole | $-CH_2-CH_2-O-CH_2-CH_2-$ | | |
| 2.15 | $n\text{-}C_3H_7-$ | $-CH_2-CH_2-O-CH_2-CH_2-$ | | |
| 2.16 | $HO-CH_2-CH_2-$ | $-CH_2-CH_2-O-CH_2-CH_2-$ | | |
| 2.17 | tert-butyl | $-CH_2-CH_2-O-CH_2-CH_2-$ | | |
| 2.18 | $n\text{-}C_{12}H_{25}-$ | $-CH_2-CH_2-O-CH_2-CH_2-$ | | |
| 2.19 | 2-ethyl-pentyl | $-CH_2-CH_2-O-CH_2-CH_2-$ | | |
| 2.20 | Benzyl | $-CH_2-CH_2-CH_2-CH_2-CH_2-$ | | |
| 2.21 | Phenyl | $-CH_2-CH_2-CH_2-CH_2-CH_2-$ | | |
| 2.22 | Cyclohexyl | $-CH_2-CH_2-CH_2-CH_2-CH_2-$ | | |
| 2.23 | Benzyl | $-CH_2-CH_2-CH_2-CH_2-$ | | |
| 2.24 | Phenyl | $-CH_2-CH_2-CH_2-CH_2-$ | | |
| 2.25 | Cyclohexyl | $-CH_2-CH_2-CH_2-CH_2-$ | | |
| 2.26 | Benzyl | $-CH_2-CH_2-N(CH_3)-CH_2-CH_2-$ | | |
| 2.27 | Phenyl | $-CH_2-CH_2-N(CH_3)-CH_2-CH_2-$ | | |
| 2.28 | Cyclohexyl | $-CH_2-CH_2-N(CH_3)-CH_2-CH_2-$ | | |
| 2.29 | Benzyl | $-CH_3$ | | |
| 2.30 | Phenyl | $-CH_3$ | | |
| 2.31 | Cyclohexyl | $-CH_3$ | | |
| 2.32 | Benzyl | $-C_2H_5$ | | |
| 2.33 | Phenyl | $-C_2H_5$ | | |
| 2.34 | Cyclohexyl | $-C_2H_5$ | | |

Example P3

2-Benzylsulfanyl-5-hydroxymethyl-thiazole a) 0.2 ml of concentrated hydrochloric acid is added to 3.0 g of 2-benzylsulfanyl-5-hydroxy-methyl-4,5-dihydrothiazol-4-ol in 25 ml of ethanol. The mixture is stirred at 50° C. for 12 hours, the solvent is removed in vacuo, and the residue is chromatographed on silica gel (ethethexane; 1:1). The title compound is obtained in the form of a yellow oil (compound 3.1).

b) 325 mg of 2-benzylsulfanyl-thiaZole-5-cathaldehyde in 35 ml of ethyl acetate are hydrogenated with 14 mg of FeCl2× 4H2O and 175 mg of platinum oxide under normal pressure for 64 hours at room temperature under a hydrogen atmosphere. The reaction mixture is filtered off and extracted with water. The organic phase is dried over sodium sulfate and concentrated in vacuo. The title compound is obtained in the form of an oil (compound 3.1).

Example P3c

The other compounds listed in Table 3 can also be prepared in a manner analogous to that described in Examples P3a and P3b.

TABLE 3

Compounds of the formula $$R-S-\underset{N}{\underset{\|}{\overset{S}{\bigvee}}}-CH_2-OH$$

| Comp. No. | R | Physical data |
|---|---|---|
| 3.1 | benzyl | oil |
| 3.2 | phenyl | |
| 3.3 | cyclohexyl | |
| 3.4 | $HO-CH_2-\text{thiazole}-S-CH_2-CH_2-$ | |
| 3.5 | $CH_2=CH-CH_2-$ | |
| 3.6 | $ClCH=CH-CH_2-$ | |
| 3.7 | $CH_2=C(CH_3)-CH_2-$ | |
| 3.8 | $CH_2=CH-CH_2-CH_2-$ | |
| 3.9 | 2-chlorobenzyl | |
| 3.10 | 4-chlorobenzyl | |
| 3.11 | $CH\equiv C-CH_2-$ | |
| 3.12 | isopropyl | |

TABLE 3-continued

Compounds of the formula $$R-S-\underset{N}{\underset{\|}{C}}\underset{S}{\overset{}{\diagdown}}-CH_2OH$$

| Comp. No. | R | Physical data |
|---|---|---|
| 3.13 | $C_2H_5-OC(=O)-CH_2-$ | |
| 3.14 | benzothiazol-2-yl | |
| 3.15 | n-$C_3H_7-$ | |
| 3.16 | $HO-CH_2-CH_2-$ | |
| 3.17 | tert-butyl | |
| 3.18 | n-$C_{12}H_{25}-$ | |
| 3.19 | 2-ethyl-pentyl | |

Example P4a

2-Benzylsulfanyl-5-hydroxymethyl-4,5-dihydrothiazol-4-ol

1.1 g of dithiocarbamic acid benzyl ester are suspended in a mixture of 6 ml of phosphate buffer (pH=7.0) and 6 ml of ethanol, and the resulting suspension is added dropwise at 0° C. to 6 ml of a 2M solution of glycidyl aldehyde in water. Stirring is carried out at room temperature for 12 hours, and then the ethanol is removed in vacuo. The aqueous phase is extracted twice with dichloromethane, and the combined organic phases are washed with saturated aqueous sodium chloride solution and dried over magnesium sulfate. After removal of the solvent, 2-benzylsulfanyl-5-hydroxymethyl-4,5dihydrothiazol-4-ol having a melting point of 80-82° C. is obtained (compound 4.1).

Example P4b

The other compounds listed in Table 4 can also be prepared in a manner analogous to that described in Example P4a.

TABLE 4

Compounds of the formula $$R-S-\underset{N}{\underset{\|}{C}}\underset{S}{\overset{}{\diagdown}}\underset{OH}{\overset{CH_2OH}{|}}$$

| Comp. No. | R | Physical data |
|---|---|---|
| 4.1 | benzyl | m.p.: 80-82° C. |
| 4.2 | phenyl | |
| 4.3 | cyclohexyl | |
| 4.4 | (4,5-dihydroxy-thiazol-2-yl)-CH₂—CH₂— | |
| 4.5 | $CH_2=CH-CH_2-$ | |
| 4.6 | $ClCH=CH-CH_2-$ | |
| 4.7 | $CH_2=C(CH_3)-CH_2-$ | |
| 4.8 | $CH_2=CH-CH_2-CH_2-$ | |
| 4.9 | 2-chlorobenzyl | |
| 4.10 | 4-chlorobenzyl | |
| 4.11 | $CH\equiv C-CH_2-$ | |
| 4.12 | isopropyl | |
| 4.13 | $C_2H_5-OC(=O)-CH_2-$ | |
| 4.14 | benzothiazol-2-yl | |
| 4.15 | n-$C_3H_7-$ | |
| 4.16 | $HO-CH_2-CH_2-$ | |
| 4.17 | tert-butyl | |
| 4.18 | n-$C_{12}H_{25}-$ | |
| 4.19 | 2-ethyl-pentyl | |

Example P5

2-Benzylsulfanyl-5-chloromethyl-thiazole (Compound 5.1)

a) To 1.4 g of 2-benzylsulfanyl-5-hydroxymethyl-4,5-dihydrothiazol-4-ol suspended in 5 ml of dichloromethane, 0.96 ml of thionyl chloride dissolved in 5 ml of dichloromethane are added dropwise at 0° C. Stirring is then carried out at room temperature for 3 hours. The mixture is diluted with 10 ml of ethyl acetate and the organic phase is washed twice with saturated aqueous sodium hydrogen carbonate solution and dried over magnesium sulfate. After removal of the solvent in vacuo, 2-benzylsulfanyl-5-chloromethyl-thiazole having a melting point of 57-61° C. is obtained.

b) To 1.18 g of 2-benzylsulfanyl-5-hydroxymethyl-thiazole dissolved in 5 ml of dichloromethane, 0.4 ml of thionyl chloride dissolved in 5 ml of dichloromethane are added dropwise at 0° C. to. The reaction mixture is then allowed to warm to room temperature and stirred for 0.5 hour. After the addition of 5 ml of water, the organic phase is washed twice with saturated aqueous sodium hydrogen carbonate solution and dried over magnesium sulfate. After removal of the solvent in vacuo, chromatography on silica gel (ether:hexane; 1:4) yields 2-benzylsulfanyl-5-chloromethyl-thiazole having a melting point of 57-61° C.

c) 5.5 ml of chloroformic acid ethyl ester are added to 8.0 g of 4-(2-benzylsulfanyl-thiazol-5-ylmethyl)-morpholine in 60 ml of tetrahydrofuran, and the mixture is heated at reflux for 5 hours. The mixture is then cooled to room temperature, the solvent is removed by evaporation in vacuo and the residue is purified by chromatography on silica gel with ether-hexane 1:2. 2-Benzylsulfanyl-5-chloromethylthiazole having a melting point of 57-59° C. is obtained.

Example P5d

The other compounds listed in Table 5 can also be prepared in a manner analogous to that described in Examples P5a to P5c.

TABLE 5

Compounds of the formula

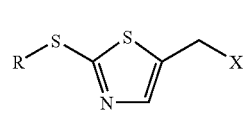

| Comp. No. | R | X | Physical data |
|---|---|---|---|
| 5.1 | benzyl | Cl | m.p.: 57-59° C. |
| 5.2 | benzyl | Br | |
| 5.3 | phenyl | Cl | |
| 5.4 | cyclohexyl | Br | |
| 5.5 | 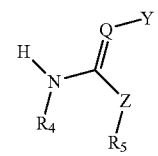 | Cl | |
| 5.6 | $CH_2=CH-CH_2-$ | Cl | |
| 5.7 | $ClCH=CH-CH_2-$ | Cl | |
| 5.8 | $CH_2=C(CH_3)-CH_2-$ | Cl | |
| 5.9 | $CH_2=CH-CH_2-CH_2-$ | Cl | |
| 5.10 | 2-chlorobenzyl | Cl | |
| 5.11 | 4-chlorobenzyl | Cl | |
| 5.12 | $CH\equiv C-CH_2-$ | Cl | |
| 5.13 | isopropyl | Cl | |
| 5.14 | $C_2H_5-OC(=O)-CH_2-$ | Cl | |
| 5.15 | 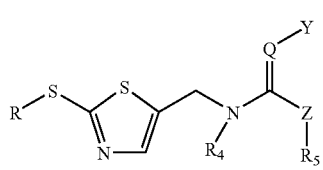 | Cl | |
| 5.16 | $n-C_3H_7-$ | Cl | |
| 5.17 | $HO-CH_2-CH_2-$ | Cl | |
| 5.18 | tert-butyl | Cl | |
| 5.19 | $n-C_{12}H_{25}-$ | Cl | |
| 5.20 | 2-ethyl-pentyl | Cl | |
| 5.21 | isopropyl | Br | |
| 5.22 | $C_2H_5-OC(=O)-CH_2-$ | Br | |
| 5.23 | 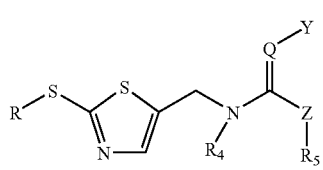 | Br | |
| 5.24 | $n-C_3H_7-$ | Br | |
| 5.25 | $HO-CH_2-CH_2-$ | Br | |
| 5.26 | tert-butyl | Br | |
| 5.27 | $n-C_{12}H_{25}-$ | Br | |
| 5.28 | 2-ethyl-pentyl | Br | |

What is claimed is:

1. A process for the preparation of a compound of the formula

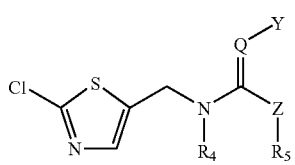
(A)

wherein

Q is CH or N; Y is $NO_2$ or CN; Z is $CHR_6$, O, $NR_6$ or S, $R_4$ and $R_5$ are either each independently of the other hydrogen or unsubstituted or $R_7$-substituted alkyl, or together form an alkylene bridge having two or three carbon atoms, and said alkylene bridge may additionally contain a hetero atom selected from the group consisting of $NR_8$, O and S;

$R_6$ is H or unsubstituted or $R_7$-substituted alkyl, $R_7$ is unsubstituted or substituted aryl or heteroaryl, and $R_8$ is H or $C_1$-$C_{12}$alkyl;

which comprises reacting a compound of formula (I)

(I)

wherein

X is a leaving group;

R is unsubstituted or substituted $C_1$-$C_{12}$alkyl or unsubstituted or substituted aryl, with a compound of the formula (B)

wherein Q, Y, Z, $R_4$ and $R_5$ are as defined above for formula (A), to form a compound of the formula (C)

wherein

R is as defined above for formula (I), and

Q, Y, Z, $R_4$ and $R_5$ are as defined above for formula (A), and converting the compound of formula (C) by means of a halogenating agent into a compound of formula (A).

* * * * *